United States Patent [19]

Kreb, III

[11] 4,043,336
[45] Aug. 23, 1977

[54] STERILE SYRINGE DEVICE

[76] Inventor: Robert J. Kreb, III, Rolling Hill Road, Skillman, N.J. 08558

[21] Appl. No.: 678,851

[22] Filed: Apr. 21, 1976

[51] Int. Cl.² ............................................. A61M 5/00
[52] U.S. Cl. .............................. 128/218 R; 128/239; 128/2 F
[58] Field of Search ....... 128/218 R, 218 NV, 218 M, 128/234, 215, 216, 272, 276, 2 F, 239, DIG. 5; 222/566, 571, 560, 561, 387, 41, 47, 48, 49

[56] References Cited

U.S. PATENT DOCUMENTS

| | | | |
|---|---|---|---|
| 2,369,304 | 2/1945 | Lewis | 128/218 R |
| 2,866,580 | 12/1958 | Nissen | 222/560 X |
| 3,143,109 | 8/1964 | Gewertz | 128/DIG. 5 |
| 3,640,431 | 2/1972 | Plumer | 222/48 |
| 3,747,812 | 7/1973 | Karman et al. | 222/387 |
| 3,848,581 | 11/1974 | Cinqualbre et al. | 128/2 F |

Primary Examiner—John D. Yasko
Attorney, Agent, or Firm—Albert Sperry; Frederick A. Zoda; John J. Kane

[57] ABSTRACT

A sterile syringe device for withdrawing or expelling fluid by means of a hypodermic needle and hermetically sealing the fluid located within the syringe, the sterile syringe including a generally cylindrically shaped housing having a plunger means therein to act as a piston to define a reservoir for the storage of fluid therein, a nipple positioned at one end of the housing to facilitate the expelling or insertion of fluid with respect to the reservoir, the nipple defining an interior passage such as a flue or the like to provide fluid flow communication between the nipple and the reservoir, the nipple adapted to have detachably affixed thereon a hypodermic needle, further including a rotationally movable outer seal positioned in abutment with the interior of an end of the housing and formed integrally with the nipple, also including a slot through which the nipple extends in order to facilitate rotational movement of the nipple and outer seal, further including an inner seal having an aperture therein selectively alignable with the flue within the outer seal for selectively preventing or allowing fluid flow communication between the hypodermic needle and the reservoir.

8 Claims, 7 Drawing Figures

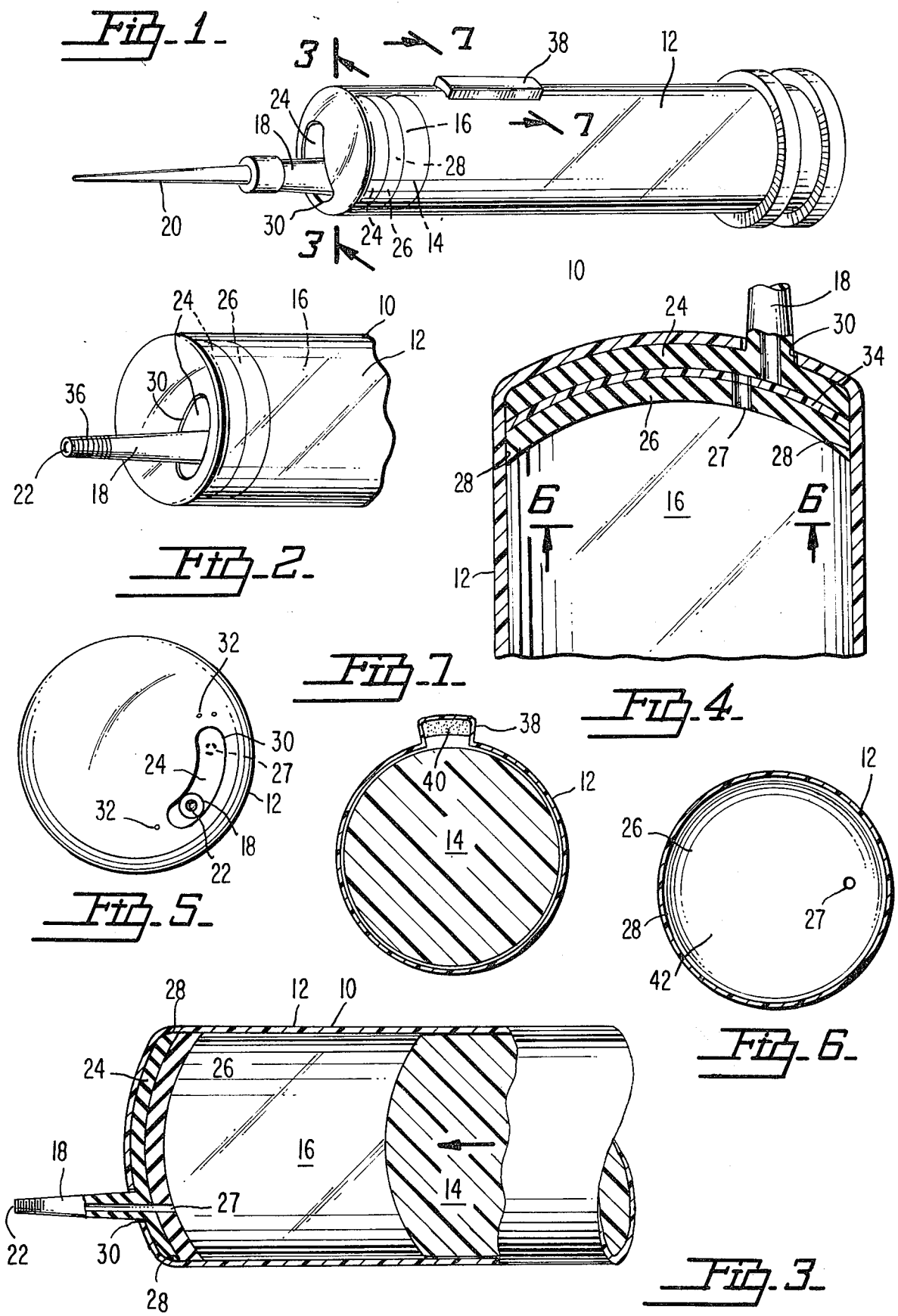

STERILE SYRINGE DEVICE

BACKGROUND OF THE INVENTION

1. Field of the Invention

The present invention deals with the field of syringe devices usable with hypodermic needle constructions. It is often convenient to construct such devices such that the portion of the hypodermic needle which penetrates the skin of the patient is disposable whereas the remainder of the syringe body is reusable. Basically, a hypodermic syringe is usable for the injection of fluids at selective locations within the soft tissues of the human body. However, it is often desirable to withdraw fluids, most usually blood or urine from the human body for various reasons.

When fluids are withdrawn by persons by the use of a hypodermic syringe, it is desirable to prevent any secondary contamination of the fluids, so withdrawn, subsequent to entering syringe body. In this respect, it is desirable to provide a means for minimizing contact between the atmosphere or any other contaminating agent and a fluid which has recently been withdrawn. In hospitals to seal a syringe, laboratory technicians, nurses and physicians often resort to bending the needle at the end of a syringe to minimize contact between the atmosphere and the withdrawn fluid. Such a procedure is initially dangerous to the technician or nurse and also does not provide an effective hermetic seal. Another attempt to maintain the withdrawn fluid in a sterile condition is to insert the needle immediately into a cork or similar device. These primitive methods have been utilized to prevent secondary contamination of withdrawn blood and the like since previously designed constructions for providing a sterile syringe have been either too costly or proved to be inefficient in operation. It would be desirable to have an effective device such as shown under the present invention which would enable the fluid within the hypodermic syringe to be sealed while the hypodermic needle is still located within the body of the patient. In this manner, secondary contamination of the reservoir within the housing of the syringe device is minimized.

2. Description of the Prior Art

Many patents have been granted on syringe devices which are usable with hypodermic needles for sealing the internal environment of the syringe device with respect to the external ambient atmosphere. One such U.S. Pat. is No. 3,872,864 issued Mar. 25, 1975 to Allen in which a plurality of internal sealible chambers is provided for use with a double syringe assembly for prefilled plastic syringes which are completely disposable. This design and those similar thereto include complicated sealing arrangements and isolating devices. Most of these designs are usable for maintaining a fluid within the syringe in an uncontaminated condition prior to insertion in the soft tissue of the human body. The present invention has a primary useful function in the field of syringes used for the withdrawing of fluids from the human body.

When fluids are withdrawn from the human body, the main problem is to place the withdrawn fluid within a culture medium for isolation of bacterial or viral contaminants. The difficulty arises when secondary contamination occurs during the transference from the syringe device to the location of the culture medium. During this critical time period, a secondary contamination could occur which would erroneously suggest the presence of a bacterial or viral entity within the blood of the subject which has entered the culture medium only by way of the secondary contamination and not as a result of being located within the body of the subject. The present invention includes a design for eliminating such secondary contaminations.

SUMMARY OF THE INVENTION

The present invention includes a standard cylindrically shaped syringe housing or chamber which cooperates with a piston or plunger means to define an interior reservoir for holding a fluid therein. At one end of the housing, the plunger means is removable longitudinally with respect thereto to draw fluid into the reservoir or to expel liquid therefrom. The outlet for fluid flow is located in the end of the syringe housing opposite from the location of the plunger means.

A slot or similar aperture may be defined by the end of the syringe housing. Positioned abutting this same end of the chamber is an outer seal member which may be made of a rubber compound or the like which includes integrally configured therewith a nipple means, which extends through the slot outwardly from the reservoir. The nipple means and the outer seal define a flue therethrough which provides a path for fluid flow communication between the reservoir and the exterior of the syringe. The nipple means may be configured to have detachably secured thereto a standard hypodermic needle or the like which may be disposable with each usage. To aid in the attachment between the hypodermic needle and the nipple means, a threaded configuration may be included in the exterior of the nipple means.

Positioned between the outer seal and the reservoir is an inner seal which may be formed of a compound similar to the outer seal. The inner seal defines therethrough an aperture which is selectively alignable with the flue defined by the outer seal. The inner and outer seals should be constructed movable with respect to one another such that the flue and the aperture may be easily aligned or misaligned. To achieve this capability, the inner and outer seals must be movable with respect to one another.

A convenient means for providing the selectively alignable feature is the cementing, heat sealing or otherwise securing of the periphery of the inner seal to the interior surface of the syringe housing. In this manner, the inner seal will cooperate with the end of the chamber to define a location in which the outer seal may be movably positioned.

Since the outer seal is formed integrally with the nipple means, the outer seal may be movable by gripping the nipple and moving it within the boundaries of the slot. In this manner, the outer seal will thereby rotate and the flue defined by the outer seal on the nipple means may be selectively positioned to register with the inner seal. By this construction, the nipple means may be moved to a location providing communication between the flue and the aperture when blood is withdrawn from a patient. As soon as blood is withdrawn and the hypodermic needle is withdrawn from the patient, the nipple can be moved to a position of non-alignment and secondary contamination of the fluid or blood withdrawn from the patient's body which is now located within the syringe will be minimized.

The syringe housing may be defined to include one or more outpouchings along the lateral surfaces thereof. The outpouchings will essentially comprise an extended cylindrical sector which may have positioned therein an "ager" or other culture medium for use in the isolation of bacterial or viral entities. By utilizing a syringe having at least one outpouching with the design of the present invention which essentially eliminates secondary contamination, an effective device may be provided for the isolation of bacteria and viruses. In addition, the device is usable with a disposable hypodermic needle system and is simple and inexpensive in construction and maintenance.

To facilitate movement of the outer seal, an interface layer may be positioned between the inner and outer seals to decrease the coefficient and friction therebetween. The most effective seals are usually formed of rubber compounds, however the coefficient of friction between two such rubber compounds is often too high to facilitate movement with respect to one another. Therefore, an interface layer may be located between the seals to decrease the coefficient of friction therebetween and facilitate movement of the nipple means within the slot.

It is often desirable to provide a syringe device which is usable by blind persons. Such persons make use of these syringes for self-innoculation for conditions such as diabetes which requires insulin injections. For use by blind persons, the slot means may include an indicator means which differentiates the ends of the slots with respect to whether the flue and aperture are aligned or not aligned. In this respect, a blind person could determine by touch whether the syringe was in a condition ready for injection. The end of the syringe housing could indicate which edge of the slot is the open position by the indicator means being in the form of protrusions or bumps in the housing being sensitive to the touch of the blind person.

It is an object of the present invention to provide a sterile syringe device for withdrawing blood and other fluids from the human body.

It is an object of the present invention to provide a sterile syringe device usable with disposable hypodermic needles.

It is an object of the present invention to provide a simple and inexpensive construction which prevents secondary contamination of fluids withdrawn from the human body.

It is an object of the present invention to provide a hypodermic syringe which includes at least one culture medium outpouching therein for the isolation of primary bacterial entities.

It is an object of the present invention to provide a sterile device for insertion of fluids into human body tissue.

It is an object of the present invention to provide a sterile syringe device for use with pre-packaged sterile fluids for effectively preventing contamination thereof.

It is an object of the present invention to provide a sterile hypodermic syringe which is usable primarily for withdrawing of fluids from the body rather than the insertion of fluids into the body.

It is an object of the present invention to provide a safe means of minimizing secondary contamination of fluids withdrawn from the human body.

It is an object of the present invention to provide a sterile syringe device which effectively increases the seal between the syringe reservoir and the external environment whenever the plunger is compressed when the seal is in a non-communicating position.

It is an object of the present invention to provide a hypodermic syringe which includes an indicator means for informing a blind person whether the sterile syringe is in a sealed or unsealed condition.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a perspective view of an embodiment of the present invention;

FIG. 2 is a perspective view of the slotted end of the syringe housing of an embodiment of the present invention;

FIG. 3 is a cross-section of FIG. 1 taken through line 3—3;

FIG. 4 is a cross-section as shown in FIG. 3 taken when the outer seal is not in a position of alignment with the aperture of the inner seal;

FIG. 5 is an end view of the embodiment shown in FIG. 2;

FIG. 6 is a cross-section of FIG. 4 taken along lines 6—6; and

FIG. 7 is a cross-section of FIG. 1 taken along lines 7—7.

DETAILED DESCRIPTION OF THE PREFERRED EMBODIMENT

An embodiment of the present invention is illustrated in FIG. 1 showing the sterile syringe device 10. A housing 12 is shown with a generally tubular configuration and a plunger means 14 positioned within the interior of the housing 12. The plunger means 14 acts as a piston within the interior chamber of the housing 12 to define a reservoir area therein in which fluid medium is contained. Access into and out of the reservoir 16 is provided by a nipple means 18 which defines therein a flue 22. The nipple means is configured to have secured thereon a hypodermic needle 20 for use in providing fluid flow communication between the reservoir and that environment from which the fluid media is to be withdrawn or into which the fluid media is to be injected.

Fluid flow communication between the reservoir 16 and the needle 20 is selectively opened or closed by the relative position of outer seal 24 and inner seal 26. Outer seal 24 is preferably integral with the nipple means 18 to define the flue 22 therethrough. Inner seal 26 is preferably configured defining an aperture 27 within which may be selectively aligned with flue 22 to create a path for fluid flow communication between the reservoir 16 and the needle 20. Inner seal 26 may be chosen fixedly positioned by securing the peripheral edge thereof to the interior walls of the housing 12. The outer seal 24 may be rotatably movable by locating a slot means 30 in the end of the housing 12 through which the nipple means extends. In this configuration as nipple means 18 is movable within the slot 30, the outer seal 24 will be movable in relationship to the fixedly positioned inner seal 26.

An embodiment of the present invention may also include a threaded section 36 of the nipple means 18 to provide a means of fixedly securing a needle 20 to the nipple 18. The usual structure of syringes having disposable hypodermic needles is to have the syringe include a rubber composition tip element such as nipple 18 onto which the disposable hypodermic needles 20 may be snugly fitted. In some structures, it may be desirable to provide a more secure attachment means and, as such, the nipple means 18 may include the threaded section 36.

The present invention may also include an interface layer 34 which will be useful in those configurations in which the coefficient of friction between the movable outer seal 24 and a stationary inner seal 26 is too great such that rotation of seal 24 is made difficult. When this situation occurs, an interface layer 34 may be positioned extending between the contacting surfaces of the seals 24 and 26 to lower the coefficient of friction therebetween. In this manner, relative movement between the movable outer seal 24 and the stationary inner seal 26 will be facilitated and rotation of the rotatable seal 24 by the movement of nipple 18 within slot 30 will be facilitated.

As an additional configuration, the external end of the syringe 10 may include indicator means 32 along each end of the slot 30. This indicator means will preferably be small protrusions at each end of the syringe such that a blind person can feel the relative position between the slot 30 and the nipple 18 and thereby be informed whether the inner and outer seals are in the aligned or non-aligned position.

Another embodiment of the present invention may include one or more outpouchings 38 defined along cylindrical sectors of the housing 12. An outpouching 38 may have located therein one or more variety of culture media 40 which will be useful in isolating bacterial or other organisms within blood, urine and other fluids withdrawn from the human body.

The present invention provides a sterile syringe device which is usable for injections into soft human body tissue as well as for the withdrawing of fluids from soft tissue as well as from other sterile environments. It is often desirable to withdraw blood from a patient or to withdraw urine from a sterile catheter such that bacterial organisms therein can be isolated. In this respect, an embodiment of the present invention may be configured having a plurality of outpouchings 38 defined by the housing 12. Each outpouching may contain therein a different culture medium as required for the isolation of those organisms to which the blood test or urine analysis is directed. In operation, as soon as the blood or urine is drawn into the reservoir area 16, the technician or nurse will rotate the nipple means 18 to the sealed position such that the aperture 27 as defined by the inner seal 26 and the flue 22 as defined by the outer seal 24 move to a non-aligning position. With this syringe configuration, the fluid which has been drawn within the reservoir 16 will be sealed hermetically from the external environment and secondary contamination thereof will be prevented. In this manner, the culture medium or media will be able to be exposed to the fluid to be tested without being repositioned to another location. In this manner, a single one-step operation for priming a culture will be achieved. Once the nipple means 18 has been moved to the sealing position, the hypodermic needle 20 may be detached from the nipple means 18 and discarded such that another disposable needle may be positioned on the nipple means 18 during the next usage of the syringe 10.

Preferably the syringe housing 12 will be formed of a transparent, plastic material such that the presence of fluid within the reservoir 16 will be apparent from an external observation of the syringe 10. As shown in FIG. 1, the housing 12 is formed from a transparent material and the inner seal 26 and the outer seal 24 may be viewed therethrough.

The inner seal 26 may be fixedly secured to the interior wall of the housing 12 by heat sealing to secure a firm connection between the housing 12 which is usually made from a plastic base material and the inner seal 26 which may be preferably made of a rubber composition. Alternatively the inner seal 26 may be cemented to the inner periphery of the housing 12.

The inner seal 26 cooperates with the inside of the end of the syringe housing 12 to define a cylindrical cross-sectional are in which the outer seal 24 is positioned. The outer seal may preferably include the nipple means 18 integrally formed therewith. In this configuration, the slot 30 will be defined by the same end of the syringe housing 12. The slot will preferably be of arcuate shape in order to allow the movement of the nipple means 18 from one end of the slot to the other end of the slot such that the conduit formed by the flue 22 and the aperture 27 may be selectively opened and closed. In this manner, a sterile syringe device is provided which is simple in construction and includes only one moving part in order to open and close the sealing means between the needle 20 and the fluid reservoir 16.

The design of the present invention includes inherent advantages for sealing communication between the needle 20 and the reservoir 16. The construction of the inner and outer seals provides a system such that if the syringe is in the sealed position with the flue and aperture not in alignment, and an attempt is made to expel liquid from the reservoir or to withdraw liquid through the needle 20 into the reservoir, the construction of the seals will increase the pressure resistant to fluid flow. In particular, if the plunger means 14 is compressed to attempt to expel fluid from the reservoir 16 at a time when the aperture and flue are not in a position of alignment, an increased fluid pressure will be exerted against the rear wall 42 of inner seal 26 and thereby create a greater force between the inner and outer seals such that fluid flow will be resisted in proportion to the increase in fluid pressure exerted by the depressing of the plunger means 14. Similarly if the plunger means 14 is withdrawn when the flue and aperture are not in a position of alignment, an increased pressure will be exerted on the outer surface of the outer seal 24 due to the difference in pressure between the external environment and the reservoir 16, such that a more effective seal between the inner and outer seals is created. In this manner, if fluid is attempting to be withdrawn when the aperture and flue are not in a position of alignment, the seals will increase their sealing quality proportionally to the amount of pressure exerted as a result of movement of the plunger means 14. One of the inherent advantages of the present invention is this ability to resist fluid flow regardless of the pressure exerted whenever the sealing means is in the non-communicating position.

While particular embodiments of this invention has been shown in the drawings and described above, it will be apparent, that many changes may be made in the form, arrangement and positioning of the various elements of the combination. In consideration thereof, it should be understood that preferred embodiments of this invention disclosed herein are intended to be illustrative only and not intended to limit the scope of the invention.

I claim:

1. A sterile syringe device comprising:

a. a syringe housing of generally cylindrical shape including an opened and a closed end, said closed end defining a slot therein, said syringe housing defining a reservoir therein;
b. a plunger means positioned within said syringe housing and being slidably movable therein to vary the volume of said reservoir;
c. nipple means positioned protruding outwardly from said reservoir and extending through said slot means in said closed end of said syringe housing, said nipple means defining a flue therein to allow fluid flow communication outward from said reservoir; and
d. sealing means positioned in the interior of said syringe housing adjacent said closed end thereof to selectively prevent and allow fluid flow communication through said flue, said sealing means further comprising:
 1. an inner seal fixedly secured to the interior walls of said housing adjacent said closed end thereof, said inner seal defining an aperture therethrough to allow fluid flow communication from said reservoir through said aperture of said inner seal to said flue within said nipple means; and
 2. an outer seal rotatably mounted with respect to said syringe housing, said outer seal being positioned between said inner seal and said closed end within said syringe housing, said outer seal being fixedly secured to said nipple means to allow rotational movement of said outer seal responsive to movement of said nipple means within said slot means, said outer seal defining an opening therethrough, said flue of said nipple means and said opening being fixedly aligned with respect to one another and being selectively alignable with respect to said aperture responsive to movement of said nipple means within said slot means to allow fluid flow communication from said reservoir through said aperture and said opening to said flue.

2. The devices as defined in claim 1 wherein said inner seal and said outer seal are made of an rubber material.

3. The device as defined in claim 1 wherein said outer seal and said nipple means are one integrally formed unit to facilitate rotational movement of said outer seal responsive to movement of said nipple means through said slot means.

4. The device as defined in claim 1 wherein said housing includes indicator means sensitive to touch adjacent each end of said slot to indicate whether said flue is aligned with said aperture.

5. The device as defined in claim 1 wherein said inner seal includes an interface layer having a lower coefficient of friction with respect to said outer seal than said inner seal to facilitate relative movement between said inner and outer seals.

6. The device as defined in claim 1 wherein said nipple means includes a threaded section to facilitate disengagement and engagement of a hypodermic needle thereto.

7. The device as defined in claim 1 wherein said inner seal is fixedly secured to said housing by being heat sealed thereto.

8. The device as defined in claim 1 wherein said inner seal is cemented to said housing.

* * * * *